United States Patent [19]

Wess et al.

[11] Patent Number: 4,977,279

[45] Date of Patent: Dec. 11, 1990

[54] PROCESS FOR THE PREPARATION OF OPTICALLY ACTIVE 3-DEMETHYLMEVALONIC ACID DERIVATIVES, AND INTERMEDIATES

[75] Inventors: Günther Wess, Erlensee; Kurt Kesseler, Bad Soden am Taunus; Ekkehard Baader, Königstein/Taunus; Gerhard Beck, Frankfurt am Main, all of Fed. Rep. of Germany

[73] Assignee: Hoechst Aktiengesellschaft, Frankfurt am Main, Fed. Rep. of Germany

[21] Appl. No.: 438,305

[22] Filed: Nov. 20, 1989

Related U.S. Application Data

[62] Division of Ser. No. 280,762, Dec. 6, 1988.

[30] Foreign Application Priority Data

Dec. 8, 1987 [DE] Fed. Rep. of Germany ....... 3741509

[51] Int. Cl.$^5$ .................. C07D 319/06; C07D 405/06; C07D 239/26
[52] U.S. Cl. .................................... 549/274; 549/333; 549/369; 549/375; 544/335; 546/268; 546/341
[58] Field of Search ............... 549/274, 333, 375, 369

[56] References Cited

U.S. PATENT DOCUMENTS 4,571,428 2/1986 Kapa ................................. 556/422

FOREIGN PATENT DOCUMENTS 0244364 11/1987 European Pat. Off. .

OTHER PUBLICATIONS

Balasubramanian et al., Chem. Abst. 111-194686g (1989).
Wess et al., Chem. Abst. 112-55602j (1990).
Lynch et al., Tetrahedron Letters, vol. 28, 1987, pp. 1385-1388.
Rosen et al., Tetrahedron Letters, vol. 42, 1986, pp. 4909-4951.
Prugh et al., Journal of Organic Chemistry, vol. 51, 1986, pp. 648-657.
Guindon et al., Tetrahedron Letters, vol. 26, 1985, pp. 1185-1188.
Sletzinger et al., Tetrahedron Letters, vol. 25, 1985, pp. 2951-2954.
Prugh et al., Tetrahedron Letters, vol. 23, 1982, pp. 281-284.
Yang et al., Tetrahedron Letters, vol. 23, 1982, pp. 4305-4308.

Primary Examiner—Cecilia Shen
Attorney, Agent, or Firm—Finnegan, Henderson, Farabow, Garrett and Dunner

[57] ABSTRACT

A process for the preparation of optically active 3-demethylmevalonic acid derivatives of the formula I

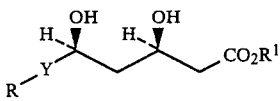

(3,5-dihydroxy carboxylic acid derivatives) or of the formula II

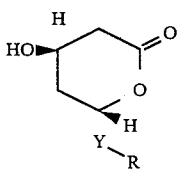

in which R, R$^1$ and Y have the indicated meanings, is described. The invention furthermore relates to aldehydes of the formula XII

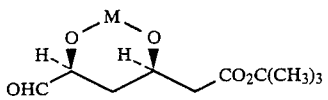

in which M represents the indicated protective groups.

1 Claim, No Drawings

PROCESS FOR THE PREPARATION OF OPTICALLY ACTIVE 3-DEMETHYLMEVALONIC ACID DERIVATIVES, AND INTERMEDIATES

This is a divisional of application Ser. No. 07/280,762 filed Dec. 6, 1988.

Derivatives of 3-demethylmevalonic acid, such as, for example, mevinolin, are of great interest as inhibitors of 3-hydroxy-3-methylglutaryl-coenzyme A reductase (HMG-CoA reductase). This enzyme catalyzes the formation of mevalonic acid from 3-hydroxy-3-methylglutaryl-coenzyme A (HMG-CoA) and, as rate-determining enzyme, plays a central part in the biosynthesis of cholesterol. Hence derivatives of 3-demethylmevalonic acid are suitable for lowering high cholesterol levels, which are associated with numerous disorders (M.S. Brown, J.L. Goldstein, Science 232, 34 (1986)). Besides the natural substance mevinolin there is a number of structurally simpler analogs (Drugs of the Future 12, 437 (1987)), which, like mevinolin, contain the demethyl-mevalonic acid structural moiety. These compounds are obtained by synthesis. The demethylmevalonir acid structural moiety is a central element of the structure of these compounds, and there is a number of processes for the synthesis thereof, as shown by the publications listed by way of example hereinafter: D.E. Lynch, R.P. Volante, R.V. Wattley, I. Shinakai, Tetrahedron Lett. 28, 1385 (1987), T. Rosen, C.H. Heathcock, Tetrahedron 42, 4909 (1986), J.D. Prugh, C.S. Rooney, A.A. Deana, H.G. Ramjit, J. Org. Chem. 51, 648 (1986), Y. Guindon, C. Yoakim, .A. Bernstein, H.E. Morton, Tetrahedron Lett. 26, 1125 (1985), M. Sletzinger, T.R. Verhoeven, R.P. Volante, J.M. McNamara, E.G. Corley, T.M.H. Liu, Tetrahedron Lett. 25, 2951 (1985), J.D. Prugh, A. Deana, Tetrahedron Lett. --23-, 281 (1982), Y.L. Yang, J.R. Falck, Tetrahedron Lett. 23, 4305 (1982). Depending on the process, the demethylmevalonic acid structural moiety is produced in two different but synthetically equivalent forms: as 3,5-dihydroxy carboxylic acid derivative I

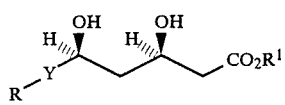

or as β-hydroxy lactone II

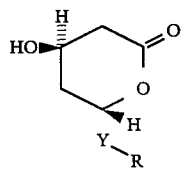

The two formulae I and II can be interconverted by known processes. Of pharmacological interest are the compounds which have the absolute configurations indicated in the formulae I and II.

The invention relates to a new process for the preparation of compounds having the demethylmevalonic acid structural moiety in the form of pure enantiomers of the formulae I and II, in which Y is the —CH=CH— or —CH$_2$—CH$_2$—group, R is a radical of the formula α

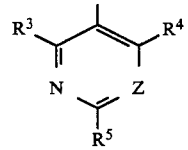

in which
Z denotes a radical of the formula —CH or a nitrogen atom,
$R^3$, $R^4$ and $R^5$ denote, independently of one another, hydrogen, a straight-chain or branched hydrocarbon radical which has up to 6 carbon atoms and can optionally be substituted at the terminal carbon by a saturated or unsaturated cyclic hydrocarbon radical having 3 to 6 carbon atoms, or denote a cyclic saturated or up to doubly unsaturated hydrocarbon radical having 3 to 7 carbon atoms, an aromatic radical selected from the group comprising phenyl, furyl, thienyl and pyridinyl, which can optionally carry in the nucleus 1 to 3 identical or different substituents from the following groups: halogen, trifluoromethyl, alkyl or alkenyl, having up to 6 carbon atoms in each case, hydroxyl, alkoxy having 1 to 6 carbon atoms, carboxyl, or carbalkoxy having 1 to 6 carbon atoms in the alkoxy moiety,
or is a radical of the formula β

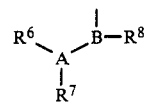

in which
A-B represents the —CH—CH—or —C=C—group
$R^6$ and $R^7$, with $R^6$ and $R^7$ being identical or different, represent a saturated or unsaturated alkyl radical which has up to 20 carbon atoms and can be substituted by an alkoxy group having 1 to 6 carbon atoms or the group

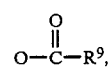

where $R^9$ denotes alkyl having 1 to 8 carbon atoms, or represent a cycloalkyl radical having 3 to 7 carbon atoms, a phenyl, thienyl, furyl or naphthyl radical, it being possible for the aromatic radicals to be substituted in the nucleus 1 to 3 times by halogen, alkyl or alkoxy, having 1 to 6 carbon atoms in each case, cycloalkyl having 3 to 7 carbon atoms or the group

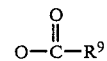

where $R^9$ denotes alkyl having 1 to 8 carbon atoms, or a pyridinyl radical which can be substituted in the nucleus 1 to 3 times by alkyl having 1 to 4 carbon atoms,
$R^8$ represents a saturated or unsaturated alkyl radical having up to 8 carbon atoms, a benzyl radical which can be substituted in the nucleus 1 to 3 times by halogen, alkoxy or alkyl, having 1 to 4 carbon atoms in each case, a phenyl, thienyl, furyl or naphthyl radical, it being possible for the aromatic radicals to be substituted in the nucleus 1 to 3 times by halogen, alkoxy or alkyl, having 1 to 4 carbon atoms in each case, or a cycloalkyl radical having 3 to 7 carbon atoms, and $R^1$ is hydrogen, a metal cation or alkyl having 1 to 8 carbon atoms.

Suitable groups R are proposed in German Patent Applications Nos. P 37 22 807.2, corresponding to U.S. Pat. application Ser. No. 216,331 (formula β), and No. P 38 23 045.3, corresponding to U.S. Pat. application Ser. No. 216,458 (formula α, priority date : Jul. 10, 1987 [Pat. application No. P 37 22 808 0], filing date Jul. 7, 1988).

Compared with the processes described, the process according to the invention represents a considerable simplification and shortening of the synthetic route.

A central intermediate for carrying out the process according to the invention is the compound of the formula III

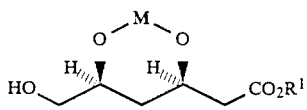

in which M is a protective group suitable for 1,3-diols, such as, for example, the $H_3C-C-CH_3$ group, or a radical of the following formulae

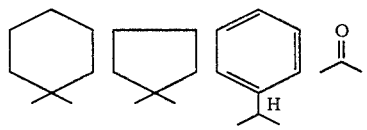

and $R^1$ denotes $C_1-C_8$-alkyl, for example t-butyl, which can ber converted into a very wide variety of derivatives of the formula I or II.

The process according to the invention comprises
(1) converting a diol ester of the formula VI

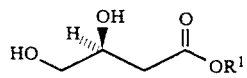

in which $R^1$ denotes $C_1-C_8$-alkyl, by introduction of a customary protective group by methods known per se into a compound of the formula VII which is protected on the primary alcohol group

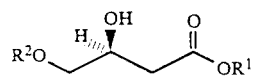

and in which $R^1$ denotes $C_1-C_8$-alkyl and $R^2$ represents a customary alcohol protective group, (2) converting a resulting compound of the formula VII, or the corresponding alcoholate thereof, by customary condensation with t-butyl acetate, or a suitable equivalent such as, for example, malonic ester, into a compound of the formula VIII

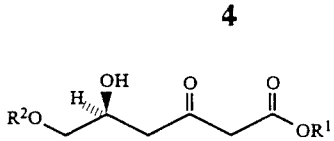

in which $R^1$ and $R^2$ have the meanings indicated for formula VII, (3) reducing a resulting hydroxy keto ester VIII by methods known per se to the 1,3-diol ester of the formula IX

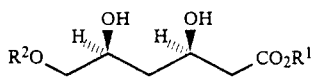

in which $R^1$ and $R^2$ have the meanings indicated for formula VII, (4) converting a resulting 1,3-diol ester of the formula IX by introduction of a protective group suitable for 1,3-diols into a compound of the formula X

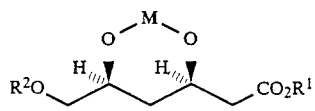

in which M is a protective group suitable for 1,3-diols, and $R^1$ and $R^2$ have the meanings indicated for formula VII, (5) converting a resulting compound of the formula X by customary methods with elimination of the protective group $R^2$ into a compound of the formula III

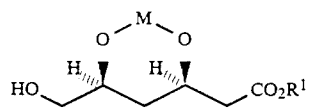

in which M is a protective group suitable for 1,3-diols, and $R^1$ denotes a $C_1-C_8$-alkyl radical, (6) converting a resulting compound of the formula III into an olefin derivative of the formula XI

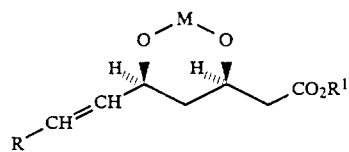

(Y of formula I = CH=CH)

and (7) hydrolyzing a resulting compound of the formula XI to give a compound of the formula I in which Y denotes the CH=CH group, and $R^1$ represents a $C_1-C_8$-alkyl radical, (8) where appropriate hydrogenating a resulting compound of the formula I in which Y represents a CH=CH group to give a compound of the formula I in which Y is the $CH_2-CH_2$ group, (9) where appropriate converting a resulting compound into the acid ($R^1$=H) or a salt ($R^1$=metal cation), and

(10) where appropriate converting a resulting compound of the formula I into a compound of the formula II.

Where $R^1$ denotes an alkyl radical having 1 to 8 carbon atoms, the alkyl racidal is straight-chain or branched.

The starting compounds of the formula VI are known or can be prepared by customary methods. The preparation expediently starts from L(—)-malic acid [S(—)-2-hydroxysuccinic acid]of the formula IV

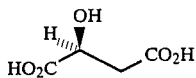  IV

This is a converted by known methods into a $C_1$–$C_8$-alkyl ester of the formula V

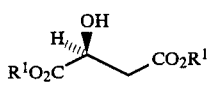  V in which $R^1$ denotes $C_1$–$C_8$-alkyl, preferably methyl or ethyl, preferably by treatment with alcohol under acidic conditions.

Compound V is reduced to the diol ester VI, preferably with borane/dimethyl sulfide complex using a catalytic amount of sodium borohydride by a process of T. Moriwake et al. (Chemistry Letters 1984, 1379).

In the process according to the invention, the diol ester VI is, in the first step, protected on the primary alcohol group. $R^2$ in the formula VII denotes an alcohol protective group (cf. Protective Groups in organic Synthesis, Wiley, N.Y. 1981), preferably t-butyldiphenylsilyl.

The condensation in step 2 is carried out with, for example, t-butyl acetate, preferably with the lithium enolate of t-butyl acetate, in a solvent at —78° C. to room temperature, preferably between —30° C. and —10° C. preferably in tetrahydrofuran (THF). 2 to 5 equivalents of the enolate are used. The lithium enolate is prepared by the customary methods, preferably using lithium diisopropylamide (LDA) at —70° C. to —50° C. One possible version of the process comprises the use of the compound VII in the form of its alcoholate, specifically as, for example, the lithium, sodium or magnesium alcoholate.

The hydroxy keto ester VIII is reduced to the 1,3-diol ester IX, specifically in such a way that the configuration indicated in formula IX is produced preferentially or exclusively.

Preferably used for this purpose is an alkylborane or alkoxyalkylborane in conjunction with sodium borohydride at temperatures between —110° C. and 0° C., specifically based on processes known from the literature (K. Narasaka, H.C. Pai, Chem. Lett. 1980, 1415, Tetrahedron Lett. 28, 155 (1987)).

Compound IX is expediently converted into the acetonide X

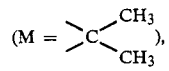

preferably using 2,2-dimethoxypropane in acetone with the addition of an acid catalyst such as, for example, p-toluenesulfonic acid.

The acetonide X is converted into the alcohol III

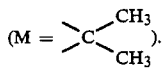

Processes known per se are used to eliminate the protective groups $R^2$. t-Butyldiphenylsilyl is preferably eliminated with fluoride ions, for example with tetrabutylammonium fluoride in THF.

The alcohol III is a valuable synthon for the preparation of demethylmevalonic acid derivatives.

To prepare the olefin derivatives of the formula XI, III is oxidized to the aldehyde XII, for example using dimethyl sulfoxide/oxalyl chloride/triethylamine (Synthesis 1981, 165)

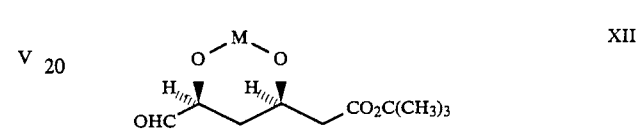  XII

The linkage of XII in which M is, for example

with a suitable halide XIII, for example for the preparation of compounds corresponding to German Patent Application No. P 38 23 045.3

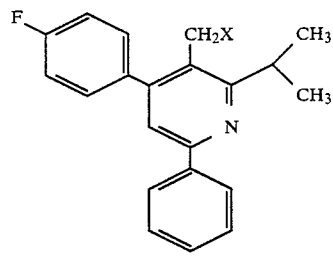

| | |
|---|---|
| X = Cl, Br | XIII |
| X = $PPh_3^+Br^\ominus$ | XIV |
| X = $PO(OAk)_2$ | XV |
| Ak = $C_1$–$C_4$-Alkyl | | is preferably carried out by a Wittig or Wittig-Horner reaction via the appropriate phosphonium halides XIV or alkyl phosphonates XV to give the compound XI' of the formula

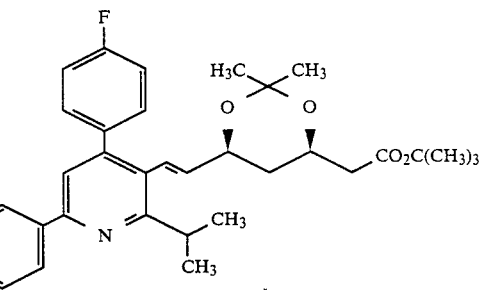  XI'

It is possible to prepare further compounds XI in an analogous manner. Compounds XI are hydrolyzed by methods known per se to give compounds I with Y=CH=CH. The conversion of a compound XI into a desired final product is illustrated hereinafter by the reaction with compound XI'. Hydrolysis of the aceonide of the formulas XI' under acidic conditions results in compound I'

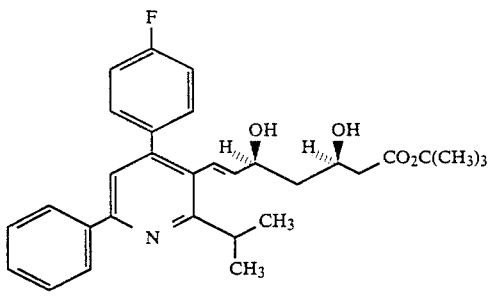

I' is converted by stasndard processes into the corresponding lactone

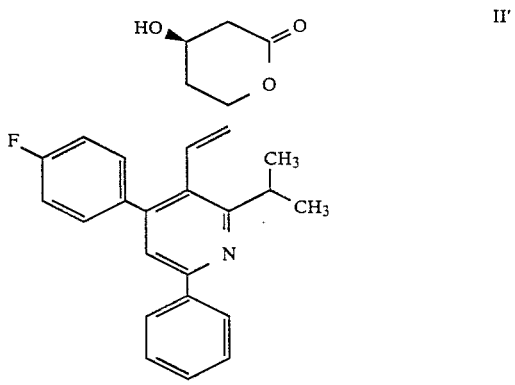

preferably with trifluoroacetic acid in methylene chloride.

The conversion of compounds I into lactones II is carried out either directly from the esters ($R^1$=$C_1$-$C_8$-alkyl) or from the corresponding free acid ($R^1$=H). Furthermore, lactones of acid-sensitive compounds are prepared from the free acids by use of lactonization reagents such as, for example, carbodiimides.

The aldehydes of the formula XII in which M denotes a radical of the formula

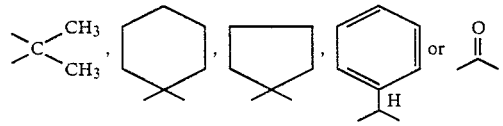

are new.

Hence the invention also relates to these compounds, and to processes for the preparation thereof. The aldehydes are, for example, valuable intermediate for the preparation of compounds of the formula I and of the formula II, which represent valuable pharmaceuticals.

EXAMPLE 1

Methyl S-3-hydroxy-4-(t-butyldiphenylsilyloxy)butyrate (formula VII)

64.05 g (0.233 mol) of t-butyldiphenylchlorosilane were added dropwise, at 0° C., to a solution of 31.1 g (0.233 mol) of methyl (3S)-3,4-dihydroxybutyrate (formula VI), Chem. Lett. 1984, 1389, and 31.7 g (0.466 mol) of imidazole in 400 ml of dry dimethylformamide. The mixture was stirred at room temperature for 2 h, then 1000 ml of water were added, and the mixture was extracted with ether (2 x). The combined organic phases were dried ($MgSO_4$) and evaporated in a rotary evaporator. Flash chromatography on silica gel (cyclohexane/ethyl acetate=3:1+1% $NEt_3$) yielded 77.4 g (0.208 mol, 89 %) of Example 1.

$[\alpha]_D^{20} = -9.6$ ° (c=10.2 in methanol)

H-NMR ($CDCl_3$), 60 MHz):$\delta$=7.80–7.20 (m, 10H), 4.20–3.60 (m, 6H). 2.5 (d. 2H), 1.05 (s, 9M)

EXAMPLE 2 t-Butyl (5S)-5-hydroxy-3-oxo-6-(t-butyldiphenylsilyloxy)-hexanoate (formula VIII)

225 ml (0.36 mol) of n-butyllithium (hexane) were added dropwise, at 0° C. under argon, to a solution of 41.0 g (0.405 mol) of diisopropylamine in 400 ml of dry THF. After 30 min at 0° C., the mixture was cooled to −70° C., and 36.7 ml (0.27 mol) of t-butyl acetate were added dropwise. After 1 h at −70° C., 27.9 g (0.075 mol) of the compound from Example 1, dissolved in a little THF, were added dropwise. After 1.5 h at −70° C., the temperature was allowed to rise slowly to −15° C. The mixture was finally stirred at −15° C. for b 15 min and then poured onto cold 500 ml of 2N HCl, 500 ml of ether. The aqueous phase was extracted 2 x with ether, and the combined organic phases were washed to neutrality with saturated sodium chloride solution (3 x). Drying with $MgSO_4$ and removal of the solvent in vacuo yielded 36 g (quantitative) of the title compound. It was transferred without further purification to the next stage.

$[\alpha]_D^{20} = -9.8°$ (c=10.6 in methanol) for the crude product.

EXAMPLE 3 t-butyl 3R,5S-dihydroxy-6-(t-butyldiphenylsilyloxy)hexanoate (formula IX)

32 ml (0.032 mol) of triethylborane solution (THF) were added dropwise, at room temperature, under argon, to 9.13 g (0.02 mol) of the compound from Example 2 in 200 ml of dry THF. After the mixture had been stirred at room temperature for 15 min it was cooled to −70° C., and 1.51 g (0.04 mol) of sodium borohydride were added, and then 15 ml of dry methanol were added. The mixture was left to stir at −70° C. for 2.5 h and was then poured into a cold solution of 35 ml of 35 percent hydrogen peroxide in 300 ml of water. Extraction was with ethyl acetate (3 x). The combined organic phases were washed with saturated sodium bicarbonate solution (3 x) and dried ($MgSO_4$). Removal of the solvent in vacuo yielded 9.48 g (quant.) of the title compound.

An analytical sample was purified by flash chromatography on silica gel (ethyl acetate/cyclohexane=2:1+1 % NEt3).

$[\alpha]_D^{20} = -6.6°$ (c=10.4 in methanol)

H-NMR (CDCl3, 270 MHz):δ=7.15 und 7.40 (each m, together 10H), 4.21 (m, 1H), 4.0 (m, 1H), 3.51 (m, 2H), 2.40 (m, 2H), 1.70–1.40 und 1.05 (several m, together 20M)

EXAMPLE 4 t-butyl (3R,5S)-6-(t-butyldiphenylsilyloxy)-3,5-O-isopropylidene-3,5-dihydroxyhexanoate (formula X)

6.88 g (0.015 mol) of the compound from Example 3 (crude product) were dissolved in 200 ml of acetone/2.75 ml of 2,2-dimethoxypropane and, at room temperature, 250 mg of p-toluenesulfonic acid were added. After 2 h at room temperature, 4 ml of triethylamine were added, and the solvent was removed in vacuo. The residue was partitioned between ether and water. The aqueous phase was extracted once with ether. The combined organic phases were washed with sodium bicarbonate solution and dried (MgSO4). Removal of the solvent in vacuo, and flash chromatography on silica gel (cyclohexane/ethyl acetate=5:1) yielded 5.2 g (0.010 mol, 70 %) of the title compound.

$[\alpha]_D^{20} = -4.0°$ ↑ (c=24.6 in methanol

H-NMR (270 MHz CDCl3):⊕=7.20 und 7.40 (each m, together 10H), 4.25 (m, 1H), 4.00 (m, 1H), 3.70 (dd, 1H), 3.52 (dd, 1H), 2.45 (dd, 1H), 2.30 (dd, 1H), 1.70 (dt, 1H), 1.50–1.00 ( different m, together 25 H)

EXAMPLE 5 t-Butyl (3R,5S)-6-hydroxy-3,5,-O-isopropylidene-3,5-dihydroxyhexanoate (formula III)

1.89 g (6 mmol) of tetrabutylammonium fluoride trihydrate were added, at 0° C., to a solution of 2.49 g (5 mmol) of the compound from Example 4 in 20 ml of THF. After 3 h at 0° C., the mixture was diluted with 100 ml of ether, and the solution was washed with 100 ml of saturated sodium chloride solution. The aqueous phase was re-extracted once with ether, and the combined organic phases were dried (MgSO4). The solvent was removed in vacuo, and the residue was flash-chromatographed on silica gel (cyclohexane/ ethyl acetate =1 : 1). Yield 1.04 g (4.0 mmol, 80%).

, $[\alpha]_D^{20} = -3.7°$ (c=14.9 in methanol

H-NMR (DMSO-d6, 270 MHz):δ=4.61 (t, 1H), 4.20 (m, 1H), 3.88 (m, 1H), 3.40–3.20 (m, 2H), 2.38 (dd, 1H), 2.22 (dd, 1H), 1.55 (dt, 1H), 1.40 (s, 12H), 1.25 (s, 3H), 1.15 (m, 1H)

MS: $C_{13}H_{24}O_5$, 261 (M+H+)

EXAMPLE 6 t-Butyl (3R,5S)-6-oxo-3,5 -O-isopropylidene-3,5-dihydroxyhexanoate (formula XII)

0.43 g (5.50 mmol) of dimethyl sulfoxide was added dropwise, at −78° C., to a solution of 0.235 ml (2.75 mmol) of oxalyl chloride in 10 ml of dichloromethane, and the mixture was stirred at the same temperature for 5 min. Then 0.65 g (2.5 mmol) of the compound from Example 5 was added dropwise. After stirring for 5 minutes, 1.70 ml of triethylamine were added, and the reaction mixture was raised to room temperature in 2 h. For working-up, the mixture was poured onto water and extracted by shaking 3 x with 50 ml of ether each time. The combined organic extracts were dried over MgSO4 and evaporated. Volatile constituents were removed from the remaining oil under high vacuum and it was immediately reacted further.

Rf (cyclohexane/ethyl acetate=1 : 1) : 0.24

Example 7

E-6S-2-(4-(4-Fluorophenyl)-2-(1-methylethyl)-6-phenylpyridin-3-yl)-ethenyl-4R-hydroxy-3,4,5,6-tetrahydro-2H-pyran2-one (formula II)

Step a: (formula XI)

1.6 ml (2.5 mmol) of a 1.6 M solution of n-butyllithium in hexane were added dropwise, at 0° C., to a solution of 0.26 g (2.5 mmol) of diisopropylamine in 10 ml of THF, and the mixture was stirred at the same temperature for 15 min. To this solution were added dropwise 1.10 g (2.5 mmol) of diethyl 4-(4-fluorophenyl)-2-(1-methylethyl)-6-phenylpyridin-3-ylmethylphosphonate (formula XV, prepared by heating the appropriate bromide with triethyl phosphite in toluene for 8 h and purification by chromatography (cyclohexane/ethyl acetate=2 : 1, silica gel)) in 5 ml of THF. The resulting deep green reaction solution was stirred at 0° C. for 1 h, and then 0.65 g of the crude product from Example 6 was added, and the mixture was stirred for 3 h to reach room temperature. For working-up, the mixture was added to 100 ml of water and extracted 3 x with 100 ml of ether each time. The combined organic phases were washed with saturated brine, dried (MgSO4) and evaporated. Flash chromatography on silica gel (cyclohexane/ethyl acetate =3:1 +1% NEt3).

H-NMR (DMSO-d6; 270 MHz):δ=0.93(mc, 2H), 1.25 (s, 3H), 1.31 (d, J=7Hz, 6H), 1.41 (s, 9H), 1.43 (s, 3H), 2.48 (mc, 2H), 3.52 (h, J=7Hz, 1H), 4.30 (mc, 1H), 4.47 (mc, 1H), 5.33 (dd, J=16Hz, 6Hz 1H), 6.56 (d, J=16Hz, 1H), 7.25 (mc, 2H), 7.40–7.53 (m. 5H), 7.66 (s,1H), 8.16 (mc, 2H) ppm MS (DCI); m/e=546 (M ⊕+H)

Step b t-Butyl E-3R,5S-3,5-dihydroxy-7-(4-(4-fluorophenyl)-2-(1-methylethyl)-6-phenylpyridin-3-yl)hept-6-enoate (formula I)

107 mg (0.19 mmol) of compound from step 7a were dissolved in 10 ml of THF, and 5 ml of 2N HCl were added. After 1.5 h at room temperature, the mixture was neutralized with saturated sodium bicarbonate solution and extracted with ether. The combined ether phases were washed once with saturated sodium chloride solution and dried (MgSO4). Removal of the solvent in vacuo and crystallization from diisopropyl ether/n-pentane yielded 78 mg (0.15 mmol, 79%).

1H-NMR (CDCl3; 270 MHz):δ=1.36 (d, J=7 Hz, 6H), 1.43–1.55 (m, 11H), 2.35 (s, 1H), 2.37 (d, J=2Hz, 1H), 3.30 (brs, 1H), 3.46 (h, J=7 Hz, 1H), 3.73 (brs, 1H), 4.11 (mc, 1H), 4.41 (mc, 1H), 5.38 (dd, J=16 Hz, 7Hz, 1H), 6.62 (dd, J=16Hz, 2 Hz, 1H), 7.08 (mc, 2H), 7.25–7.49 (m, 6H), 8.10 (mc, 2 H)

MS: (FAB): m/e 32 506 (M⊕+H)

Step c

E-6S-2-(4-(4-fluorophenyl)-2-(1-methylethyl)-6-phenyl-pyridin-3-yl)ethenyl-4R-hydroxy-3,4,5,6-tetrahydro-2H-pyran-2-one (formula II)

A solution of 41 mg (0.08 mmol) of compound from step b in 2 ml of dichloromethane and 0.10 ml (0.59 mmol) of trifluoroacetic acid was stirred at room temperature, monitoring the progress of the reaction by thin-layer chromatography (silica gel, cyclohexane/ethyl acetate=2:1). Precursor was no longer present after 8 h. The reaction solution was added to saturated NaHCO$_3$ solution and extracted several times with ether. The combined organic extracts were washed with water, dried (MgSO$_4$) and evaporated. The residue was 40 mg (100%) of Example 7, which agrees in all characteristics with authentic material (cf. German Patent Application No. P 38 23 045.3).

Step d

The corresponding sodium salts are obtained from the esters from step b

Sodium E-3R,5S-3,5-dihydroxy-7-(4-(4-fluorophenyl)-2-(1-methylethyl)-6-phenylpyridin-3-yl)hept-6-enoate 1 mmol of ester from step b is hydrolyzed with 1 mmol of sodium hydroxide solution in ethanol/water at room temperature. The solvent is removed in vacuo, and the residue is azeotroped several times with toluene. The residue is triturated with ether/hexane.

The following compounds of the formula I or II can be prepared in an analogous manner:

sodium E-3R,5S-9,9-di(4-fluorophenyl)-3,5-dihydroxy-8-isopropyl-6,8-nonadienoate sodium E-3R,5S-9,9-di(4-fluoro-3-methylphenyl)-3,5-dihydroxy-8-isopropyl-6,8-nonadienoate sodium E-3R,5S-9,9-di(4-fluoro-2-methylphenyl)-3,5-dihydroxy-8-isopropyl-6,8-nonadienoate sodium E-3R,5R-9,9-di(4-fluoro-3-methylphenyl)-3,5-dihydroxy-8-isopropyl-8-nonenoate sodium E-3R,5R-9,9-di(4-fluorophenyl)-3,5-dihydroxy-8-isopropyl-8-nonenoate E-6S-(2-(4-(4-fluorophenyl)-2-(1-methylethyl)-6-phenylpyridin-3-yl)ethenyl)-4R-hydroxy-3,4,5,6-tetrahydro-2H-pyran-2-one E-6S-(2-(2,6-bis(1-methylethyl)-4-(4-fluorophenyl)-pyridin-3-yl)ethenyl)-4R-hydroxy-3,4,5,6-tetrahydro-2H-pyran-2-one E-6S-(2-(6-(1,1-dimethylethyl)-4-(4-fluorophenyl)-2-(1-methylethyl)pyridin-3-yl)ethenyl)-4R-hydroxy-3,4,5,6-tetrahydro-2H-pyran-2-one E-6S-(2-(4,6-bis(4-fluorophenyl)-2-(1-methylethyl)-pyridin-3-yl)ethenyl)-4R-hydroxy-3,4,5,6-tetrahydro-2H-pyran-2-one E-6S-(2-(2-(4-fluorophenyl)-4-(1-methylethyl)-6-phenylpyridin-3-yl)ethenyl)-4R-hydroxy-3,4,5,6-tetrahydro-2H-pyran-2-one E-6S-(2-(6-(2,5-dimethylphenyl)-4-(4-fluorophenyl)-2-(1-methylethyl)pyridin-3-yl)ethenyl)-4R-hydroxy-3,4,5, 6-tetrahydro-2H-pyran-2-one 6S-(2-(2-ethyl-4-(4-fluorophenyl)-6-phenylpyridin-3-yl)-ethyl)-4R-hydroxy-3,4,5,6-tetrahydro-2H-pyran-2-one E-6S-(2-(2-cyclohexyl-4-(4-fluorophenyl)-6-(1-methylethyl) pyridin-3-yl)ethenyl)-4R-hydroxy-3,4,5,6-tetrahydro-2H-pyran-2-one E-6S-(2-(4-(4-fluorophenyl)-2-(1-methylethyl)-6-phenylpyrimidin-3-yl)ethenyl)-4R-hydroxy-3,4,5,6-tetrahydro-2H-pyran-2-one E-6S-(2-(2,6-bis(1-methylethyl)-4-(4-fluorophenyl)-pyrimidin-3-yl)ethenyl)-4R-hydroxy-3,4,5,6-tetrahydro-2H-pyran-2-one E-6S-(2-(6-cyclohexyl-4-(4-fluorophenyl)-2-(1-methylethyl) pyrimidin-3-yl)ethenyl)-4R-hydroxy-3,4,5,6-tetrahydro-2H-pyran-2-one E-6S-(2-(4,6-bis(4-fluorophenyl)-2-(1-methylethyl)-pyrimidin-3-yl)ethenyl)-4R-hydroxy-3,4,5,6-tetrahydro-2H-pyran-2-one

What is claimed is:

1. An aldehyde of the formula XII

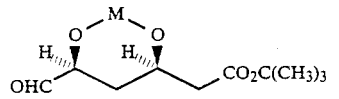

in which M denotes a radical of the formula

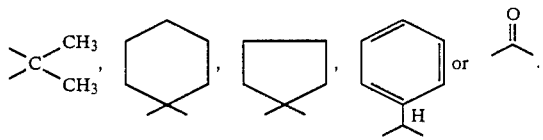

* * * * *